United States Patent
Rygaard

[11] Patent Number: 5,954,735
[45] Date of Patent: Sep. 21, 1999

[54] METHOD AND ANASTOMOTIC INSTRUMENT FOR USE WHEN PERFORMING AN END-TO-SIDE ANASTOMOSIS

[75] Inventor: Jørgen A. Rygaard, Gentofte, Denmark

[73] Assignees: Oticon A/S, Hellerup, Denmark; Bernafon AG, Berne, Switzerland

[21] Appl. No.: 09/125,678
[22] PCT Filed: Feb. 29, 1996
[86] PCT No.: PCT/DK96/00087
§ 371 Date: Aug. 24, 1998
§ 102(e) Date: Aug. 24, 1998
[87] PCT Pub. No.: WO97/31575
PCT Pub. Date: Sep. 4, 1997

[51] Int. Cl.$^6$ .................................................. A61B 17/04
[52] U.S. Cl. ............................................................. 606/153
[58] Field of Search .................................... 606/153, 154, 606/155, 152, 219, 151

[56] References Cited

U.S. PATENT DOCUMENTS

| | | | |
|---|---|---|---|
| 3,040,748 | 6/1962 | Klein et al. .............................. | 606/153 |
| 3,519,187 | 7/1970 | Kapitanov et al. . | |
| 4,076,162 | 2/1978 | Kapitanov et al. . | |
| 4,523,592 | 6/1985 | Daniel ...................... | 606/153 |
| 4,747,407 | 5/1988 | Liu et al. ................................ | 606/153 |
| 5,205,459 | 4/1993 | Brinkerhoff et al. . | |
| 5,292,053 | 3/1994 | Bilotti et al. . | |
| 5,366,462 | 11/1994 | Kaster et al. . | |
| 5,403,333 | 4/1995 | Kaster et al. ........................... | 606/151 |
| 5,695,504 | 12/1997 | Gifford, III et al. ..................... | 606/153 |
| 5,707,380 | 1/1998 | Hinchliffe et al. ....................... | 606/153 |

Primary Examiner—Gary Jackson
Attorney, Agent, or Firm—Larson & Taylor

[57] ABSTRACT

An anastomotic instrument (201) and a method for establishing an end-to-side anastomosis. The instrument includes an anvil assembly (202A, 203, 203A), having stapling recesses (204), a clamping assembly (205B, 205A) adapted to be advanced towards the rear face of the anvil (203), and a stapling assembly (206, 206A), to be moved towards the anvil (203). All three assemblies can be split along a common dividing surface, and during the operation, the separable parts of the assemblies are held together by a common elastic rubber sheath (410), to ensure a correct sequence of relative movement when the three assemblies are pressed together by a manual implement having jaws (202C, 206C). After the anastomosis has been established, the rubber sheath (410) may be cut open to enable the separable parts to be separated from each other.

9 Claims, 12 Drawing Sheets

METHOD AND ANASTOMOTIC INSTRUMENT FOR USE WHEN PERFORMING AN END-TO-SIDE ANASTOMOSIS

TECHNICAL FIELD

The present invention relates to a method and instrument for connecting an end region of a first vessel to the side of a second vessel by carrying out an end-to-side anastomosis.

BACKGROUND ART

A method closely related to the one referred to above is described in the international application WO-A-97/16122. In this previous method, the various relatively movable assemblies, viz. the anvil assembly, the clamping assembly and the stapling assembly, extended circumferentially all the way around the internal space in the instrument accommodating the first vessel or graft vessel, for which reason it was necessary when removing the instrument from the anastomosis having been established to move it along the graft vessel to the latter's free end or to pull the graft vessel out of the instrument.

This means, of course, that the instrument of said application WO-A-97/16122 can only be used with totally free graft vessels leaving one free end after anastomosis, making it possible to use the instrument for establishing anastomoses at both ends of an originally free graft vessel—or at the only free end of a closely situated anatomical artery (typically, but not exclusively the Internal Mammarian Artery—the socalled IMA vessel), such as may be required in coronary surgery.

U.S. Pat. No. 3,519,187 and U.S. Pat. No. 4,076,162 disclose methods comprising the use of instruments for connecting an end region of a first vessel to the side of a second vessel by carrying out an end-to-side anastomosis, in which the anvil assemblies can be split lengthwise. This is not, however, sufficient to overcome the limitation explained above, as other active assemblies necessitate having a free end on the graft vessel to enable them to be removed.

DISCLOSURE OF THE INVENTION

It is the object of the present invention to provide a method of the kind referred to above, with which it is possible to use the instrument for establishing anastomoses at any free end of a graft vessel, such as may be required in coronary surgery, and this object is achieved by proceeding as set forth hereinbelow. In this manner, all active parts of the instrument may be divided along the internal space accommodating the graft vessel, the two parts arising out of this dividing being removable sideways from the graft vessel, so that the latter does not necessarily have to have a free end.

The present invention also relates to an anastomotic instrument for carrying out the method according to the invention. This instrument is for connecting an end region of a first vessel to the side of a second vessel by carrying out an end-to-side anastomosis, corresponding to the Prior Art as disclosed in the above-mentioned U.S. Pat. No. 3,519,187, and according to the invention, it also comprises the features set forth hereafter.

Advantageous embodiments of the method and the anastomotic instrument according to the invention, and the effects of which (beyond what is self-evident) are explained in the following detailed part of the present description.

BRIEF DESCRIPTION OF THE DRAWINGS

In the following detailed part of the present description, the invention will be explained in more detail with reference to the exemplary embodiments of an anastomotic instrument according to the invention shown in the drawings, in which.

DESCRIPTION OF THE PREFERRED EMBODIMENTS

As mentioned above, the embodiment shown in FIGS. 1–8 of the anastomosis instrument according to the invention subject of the application WO-A-97/16122 constitutes a simplified version with the primary purpose of explaining the invention; this does not, however, preclude the possibility of using this embodiment in actual practice.

Figure 1:
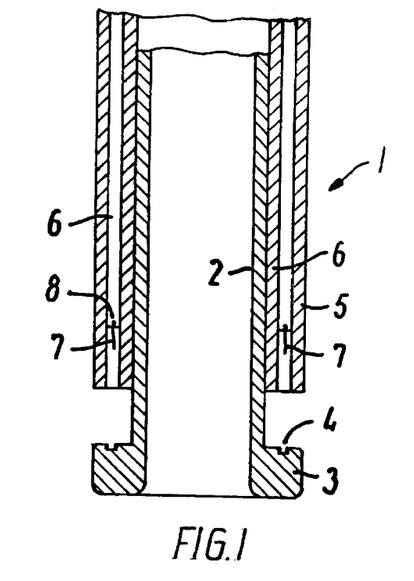
FIGS. 1–8 show the process of performing an end-to-side anastomosis using an anastomotic instrument according to the invention subject of the application WO-A-97/16122 referred to initially, FIGS. 1–7 being drawn in a highly simplified manner for ease of understanding, FIGS. 9–12 in perspective and with certain parts cut away show a practical embodiment of an anastomotic instrument according to the aforesaid invention with the various possible relative positions of the relatively movable parts, FIG. 13 at a highly enlarged scale shows a part of the instrument shown in FIG. 1 with modified clamping surfaces.

Thus, FIG. 1 shows an anastomosis instrument 1 consisting of three main components that are movable relative to each other in the longitudinal direction, i.e. in the direction shown as the vertical direction in FIG. 1:

an anvil tube 2, a clamping tube 5, and a set of stapling plungers 6.

On its lower end, the anvil tube 2 carries an anvil 3, the upper side of which is provided with a number of staple-bending recesses 4 adapted to cooperate with and bend an equal number of staples 7, in the situation shown in FIG. 1 being temporarily held lightly in an equal number of staple-holding recesses 8 formed in the lower ends of the stapling plungers 6.

Figure 2:
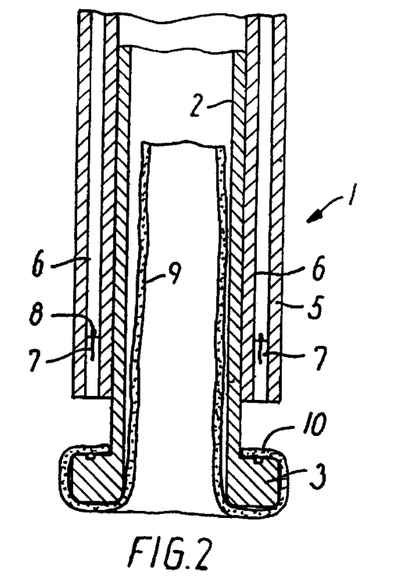

FIG. 2 shows the situation, in which the instrument is made ready for use by the operating surgeon. As mentioned initially, the anastomosis instrument shown is primarily developed for use when performing coronary bypass operations, and to this end, a bypass vessel 9—that may be a vein taken from some other part of the patient's body—has been inserted in the anvil tube with its lower end everted about the anvil 3 and with its end region 10 covering the staple-bending recesses 4 in the upper surface of the anvil 3. At this point it should be noted that the bypass vessel 9 may have a considerably larger circumference than the inside of the anvil tube 2, consequently lying more or less folded in the longitudinal direction in the latter, for which reason the action of everting its end region 10 about the anvil 3 does not necessarily entail undue stretching of the bypass vessel 9.

Figure 3:
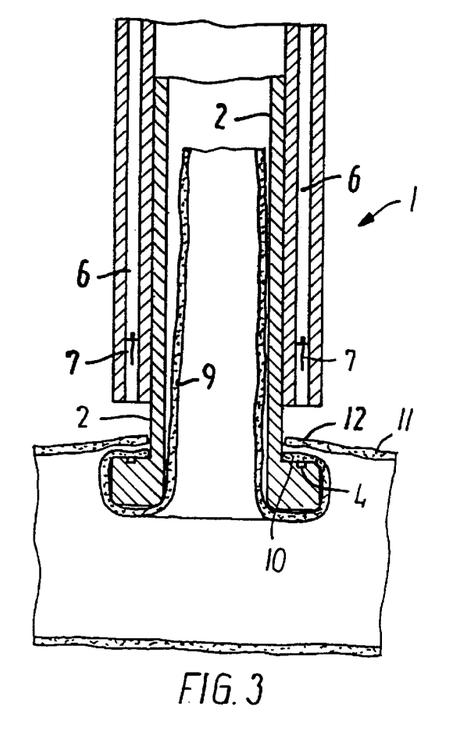

FIG. 3 shows the instrument having been made ready as shown in FIG. 2 inserted in an opening in a coronary artery 11, said opening having an edge region 12 which, due to the elasticity of the tissue of the coronary artery 11, will embrace the anvil tube 2 in a location close to the anvil 3. The opening in the coronary artery 11 may e.g. have been formed according to the method described in the international application with publication No. WO 95/17127 with the title "Method and instrument for establishing the receiving side of a coronary artery bypass graft".

Figure 4:
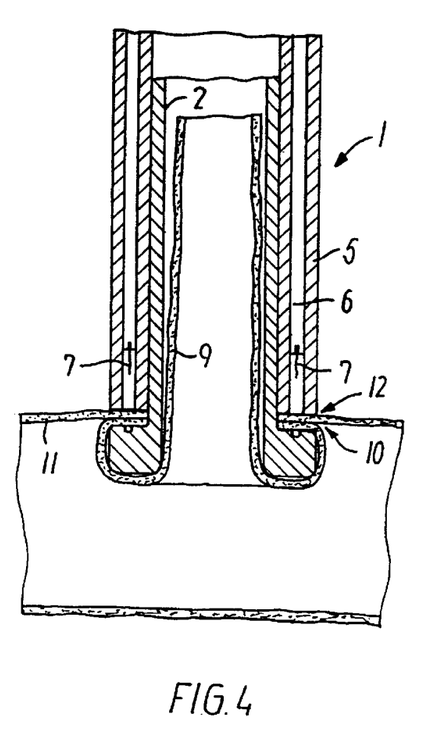
Figure 5:
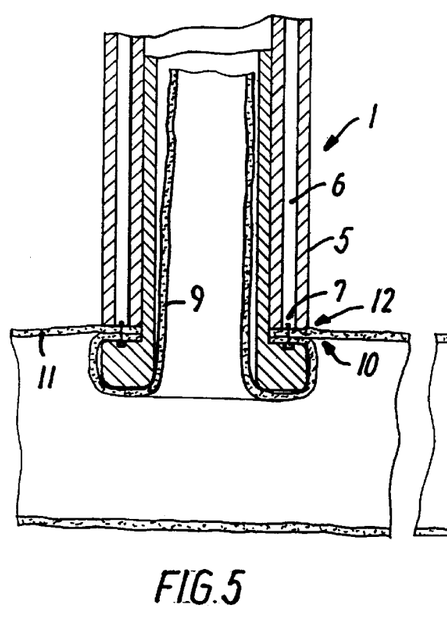

As soon as the operating surgeon in the situation shown in FIG. 3 has ascertained that the edge region 12 embraces the anvil tube 2 closely on all sides, he or she will proceed to the situation shown in FIG. 4, in which the clamping tube 5 has been moved towards the anvil 3 so as to clamp the edge region 12 on the coronary artery 11 and the end region 10 on the bypass vessel 9 firmly together in readiness for the next step shown in FIG. 5, in which the stapling plungers 6 have been moved downwardly so as to cause the staples 7 to penetrate the edge region 12 and the end region 10 and engage the staple-bending recesses 4, by which they will be bent in a tangential direction in a similar manner as is known from both surgical staplers and ordinary office staplers.

Figure 6:
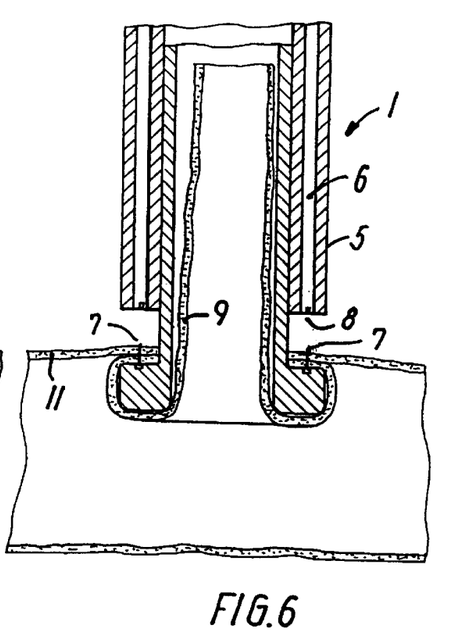

In the situation shown in FIG. 6, the clamping tube 5 together with the stapling plungers 6 have been moved outwardly and away from the staples 7, the staple-holding recesses 8 due to their light holding action having let go of the staples 7, the latter also having been anchored in the end region 10 by their bent ends.

Figure 7:
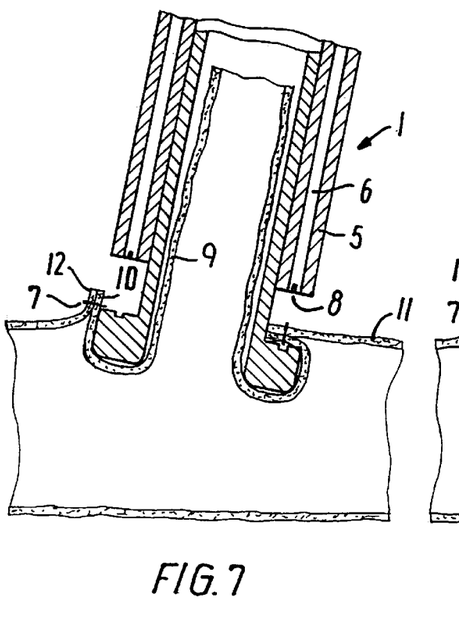
Figure 8:
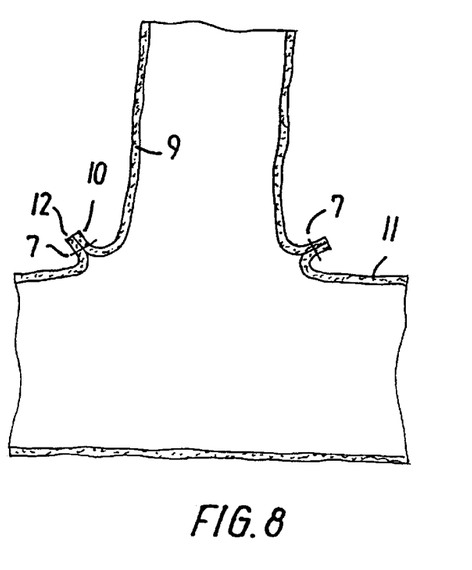

FIG. 7 shows the situation, in which the operation of removing the anastomosis instrument 1 from the coronary artery 11 and its anastomosis with the bypass vessel 9 has begun. As will be seen from FIGS. 6 and 7, the circumferential pocket formed by the eversion of the lower end of the bypass vessel 9 will now open and allow the anvil 3 to be removed by luxation, FIG. 8 showing the situation after such removal, resulting in a finished anastomosis of the intima-to-intima type considered most desirable for this type of operation.

The three main components of the anastomosis instrument 1 referred to above, i.e. the anvil tube 2, the clamping tube 5 and the set of stapling plungers 6, will, of course, have to be connected to some kind of operating members to enable the operating surgeon and his or her assistants to carry out the steps shown in FIGS. 1–8. Theoretically, these operating members could consist of three tubes (not shown), viz.

a relatively long holding tube in continuation of the anvil tube 2, a somewhat shorter clamping tube in continuation of the clamping tube 5, and an even shorter stapling tube, to which the stapling plungers 6 are connected.

As is well-known, however, coronary bypass operations, especially according to the method subject to the international application No. WO 95/17127 entitled "Method and instrument for establishing the receiving site of a coronary artery bypass graft", should be carried out as rapidly as possible, and for this reason, the "theoretical" embodiment shown in FIGS. 1–7 is too cumbersome to work with to ensure a sufficiently rapid operating procedure. As mentioned above, FIGS. 9–12 illustrate an embodiment of an anastomosis instrument, that is highly suitable for creating an end-to-side anastomosis in a very short time.

Due to the construction of the instrument shown in FIGS. 9–12 it is not possible to make an easily understandable drawing in the nature of the simple drawings of FIGS. 1–7. For this reason, the "active" parts of the instrument have been shown in perspective, and with the exception of the anvil and its supporting columns, with one half removed along a longitudinal sectional plane, so that the remaining half can be seen partly from the inside, partly from the outside. In FIGS. 9–12, those of the components functionally corresponding to components shown in FIGS. 1–7 have been given the same reference numbers with 100 added, whereas components not having "opposite numbers" in FIGS. 1–7 have been given the reference numbers of the components, with which they are most closely associated, with the addition of a capital letter.

Figure 9:
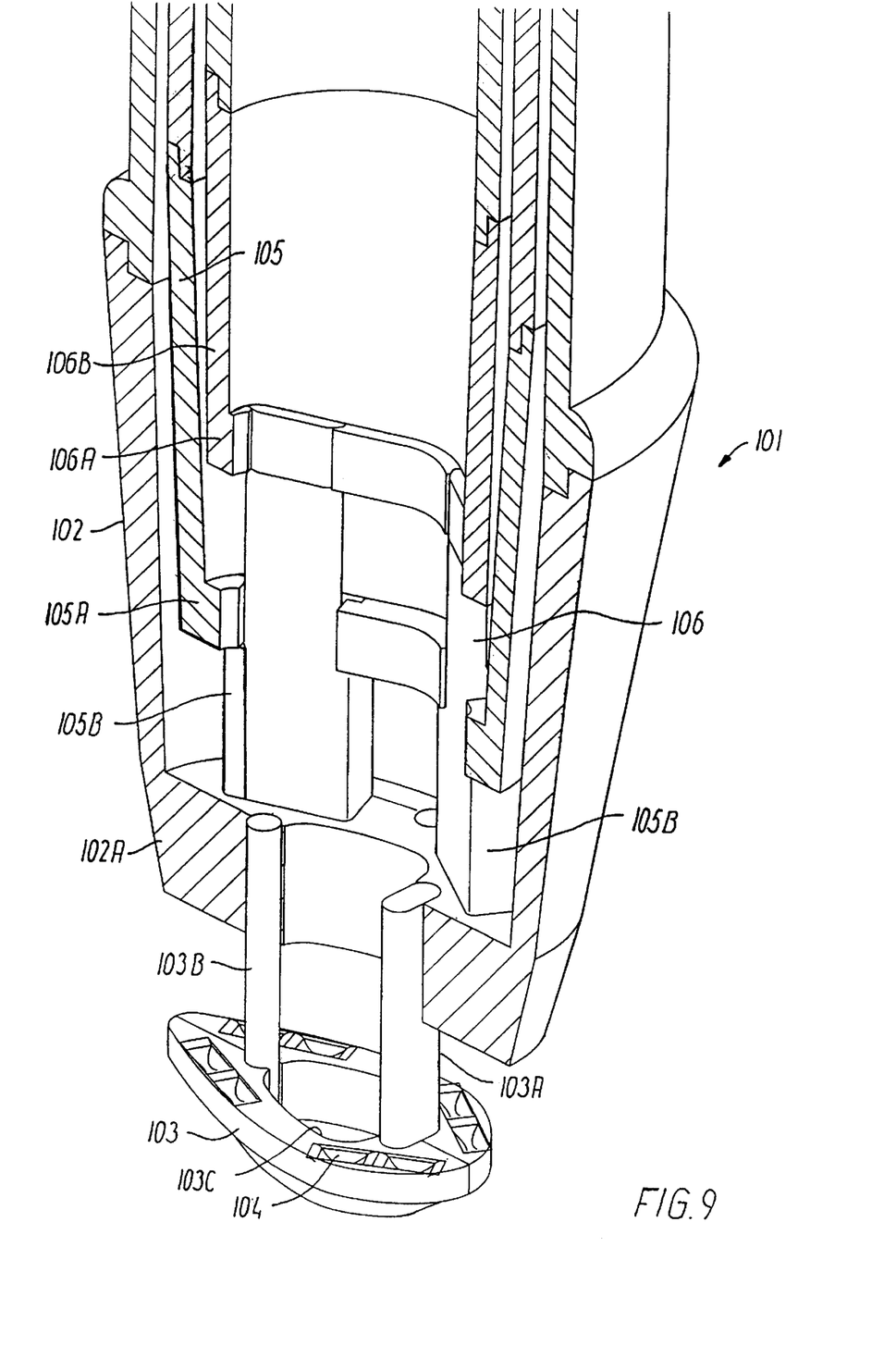

As shown in FIG. 9, the anastomosis instrument 101 comprises a number of parts functionally corresponding to parts of the instrument shown in FIGS. 1–7, viz.:

an anvil tube 102, an anvil 103, a clamping tube 105, and a set of stapling plungers 106.

Although the basic functions of these parts are the same as the basic functions of the corresponding parts in the embodiment of FIGS. 1–7, the arrangement differs somewhat from that of the latter, as will be evident from the following.

In contrast to the anvil tube 2 of FIG. 1, the anvil tube 102 of FIG. 9 extends on the outside of the instrument and is terminated by an end wall 102A, to which the anvil 103 is secured at a distance by means of two columns, viz. an upstream column 103A and a downstream column 103B. The expressions "upstream" and "downstream" to the direction of blood flow in the artery, in which the instrument 101 will normally, but not necessarily exclusively, be used in creating an end-to-side anastomosis.

To make it possible to insert the bypass vessel (not shown) corresponding to the bypass vessel 9 shown in FIGS. 1–8, all transversely oriented components have suitable openings, of which the forwardmost opening 103C is formed in the anvil 103, the latter being provided with staple-bending recesses 104 having the same function as the staple-bending recesses 4 shown in FIG. 1.

As will be seen from FIGS. 9–12, the various components are not rotationally symmetrical about the longitudinal axis of the instrument, as the anvil 103 has been made "boat-shaped" to make it easier to insert it in the opening in the artery and to make it easier for the edges of the opening to fit in with the upper side of the anvil 103 with the stapling recesses 104.

Due to the arrangement of the anvil tube 102 as the outermost component terminated by the end wall 102A, it is not possible in this embodiment to let the clamping tube 105 extend in its full circumferential width all the way towards the upper face of the anvil 103. For this reason, the clamping tube 105 is terminated by an end wall 105A, from which a set of clamping columns 105B extend in the forward (downward) direction through suitable openings in the anvil tube end wall 102A.

The stapling plungers 106 are guided in the longitudinal direction in suitable guides in the clamping columns 105B, and their rearmost (uppermost) ends are secured to a stapling plunger carrier 106A, itself secured to and terminating a stapling tube 106B, through which the force for actuating the stapling plungers 106 may be transmitted from a suitable operating device. FIGS. 9–12 show neither staples corresponding to the staples 7 of FIG. nor staple-holding recesses corresponding to the staple-holding recesses 8 shown in FIG. 1, but it will be understood that the forwardmost (lowermost) ends of the stapling plungers 106 will be provided with suitable staple-holding recesses capable of holding staples in such a position, that when the stapling plungers 106 are advanced towards the anvil 103, the staples will be bent by the staple-bending recesses 104 in the usual manner.

The relative positions of the various parts as shown in FIG. 9 correspond to those shown in FIGS. 1–3, i.e. there is a sufficient distance between the rearward (upper) face of the anvil 103 and the forward (downward) ends of the clamping columns LOSB to accomodate the everted end region of the bypass vessel corresponding to the end region 10 shown in FIG. 2, as well as the edge region of the coronary artery concerned corresponding to the edge region 12 of the coronary artery 11 shown in FIG. 3.

Figure 10:
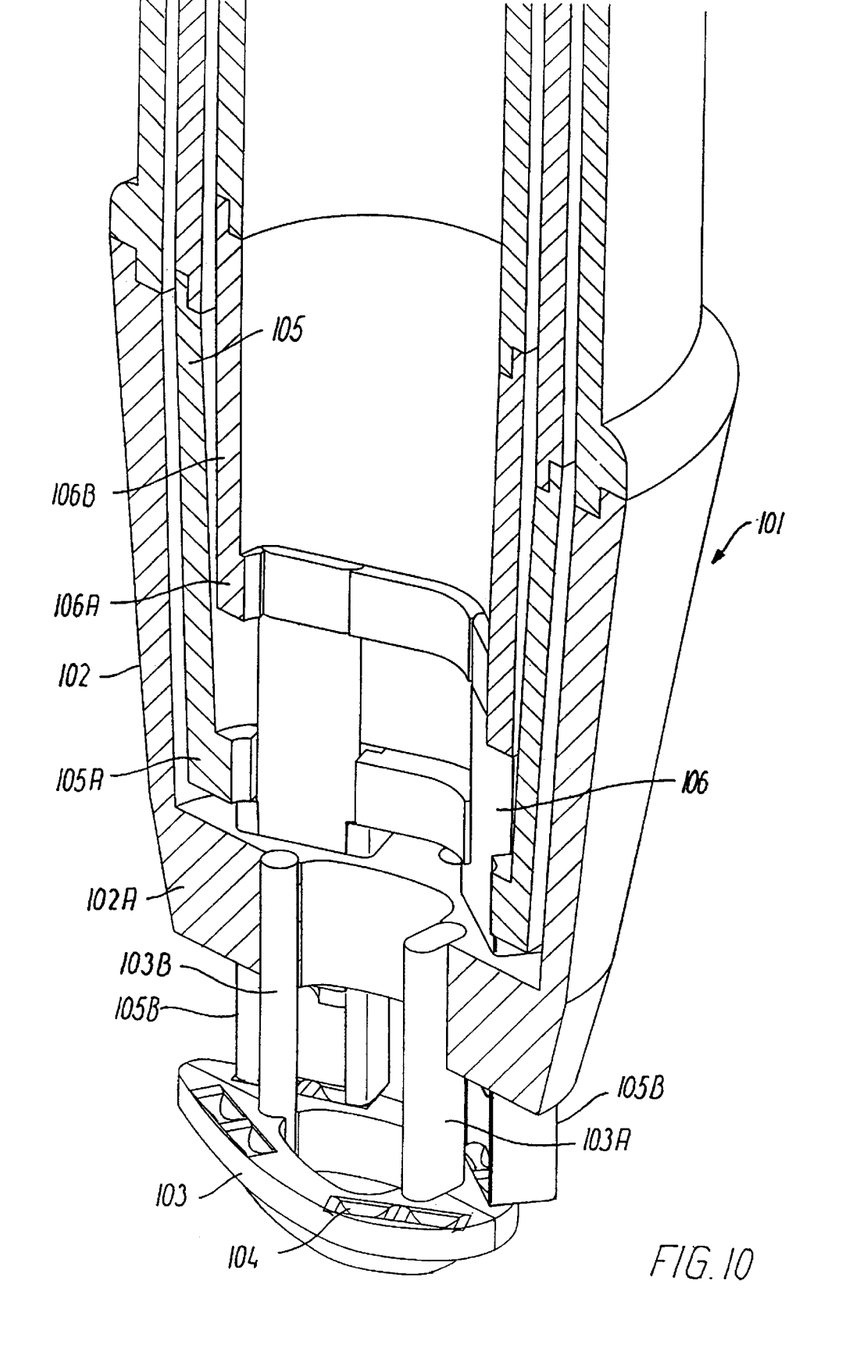

The situation shown in FIG. 10 corresponds to that shown in FIG. 4, i.e. the clamping columns 105B have been advanced towards the anvil 103, in FIG. 10 leaving a gap symbolizing the presence of the end region of the bypass vessel and the edge region of the coronary artery (all not shown). The movement of the clamping columns 105B has, of course, been effected by advancing the clamping tube 105 to the same extent. To prevent said end and edge regions being crushed in the clamping operation, suitable stops (not shown) are adapted to stop the movement of the clamping columns 105B towards the anvil 103 so as to leave a gap just sufficient to hold them firmly together. To improve the grip, the clamping surfaces may be provided with elastically flexible fins or fingers. FIG. 13 shows how this concept could be applied to the embodiment shown in FIGS. 1–7, it being—of course—equally applicable to that shown in FIGS. 9–12, or the apparatus according to the present invention shown in FIGS. 14–18 and described below.

Figure 11:
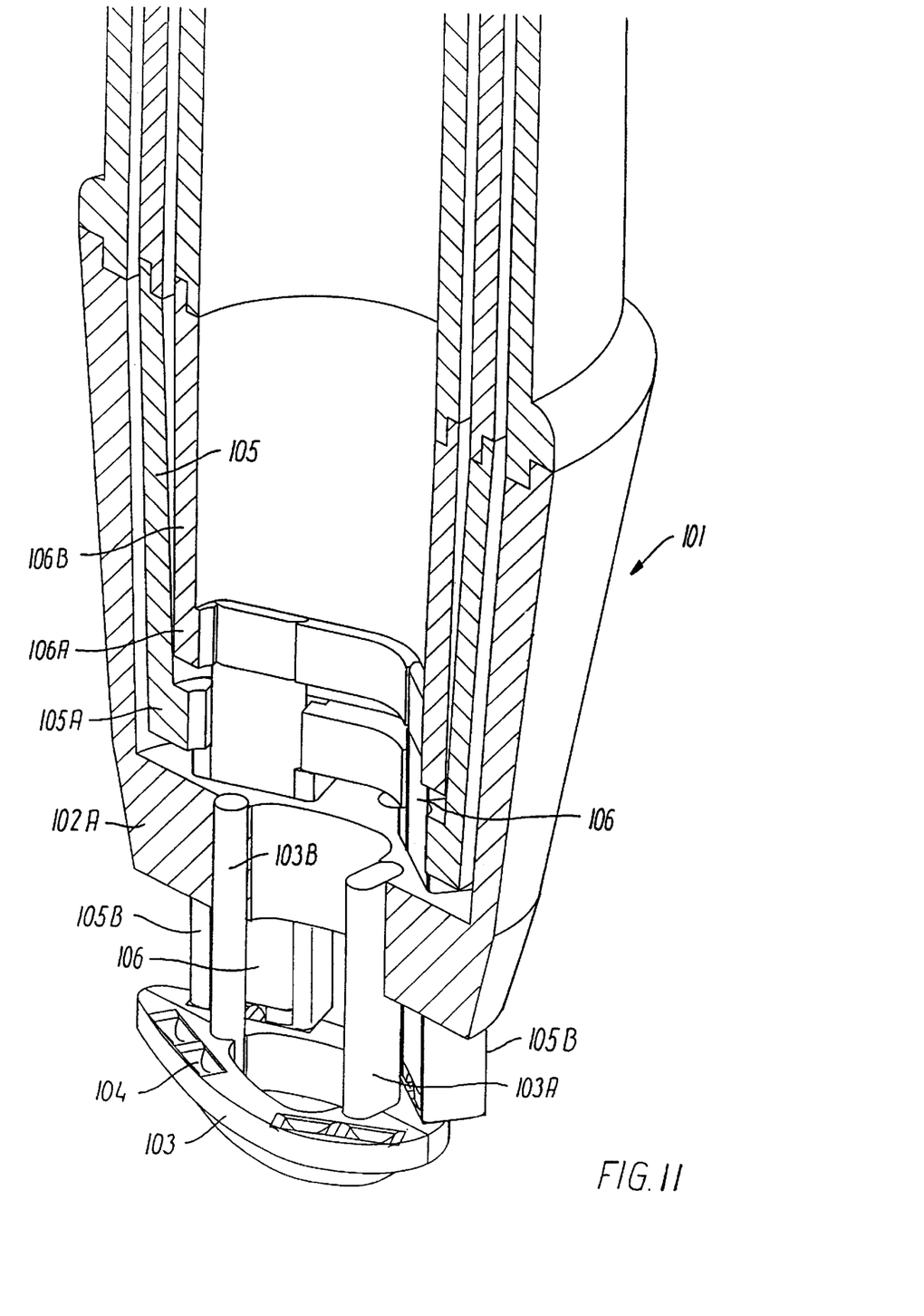

The relative positions shown in FIG. 11 correspond to those shown in FIG. 5, i.e. the stapling plungers 106 have now been advanced, guided by the clamping columns 105B so as to bring the staples (not shown) into engagement with the staple-bending recesses 104, thus joining the end region of the bypass vessel to the edge region of the coronary artery (all not shown).

Figure 12:
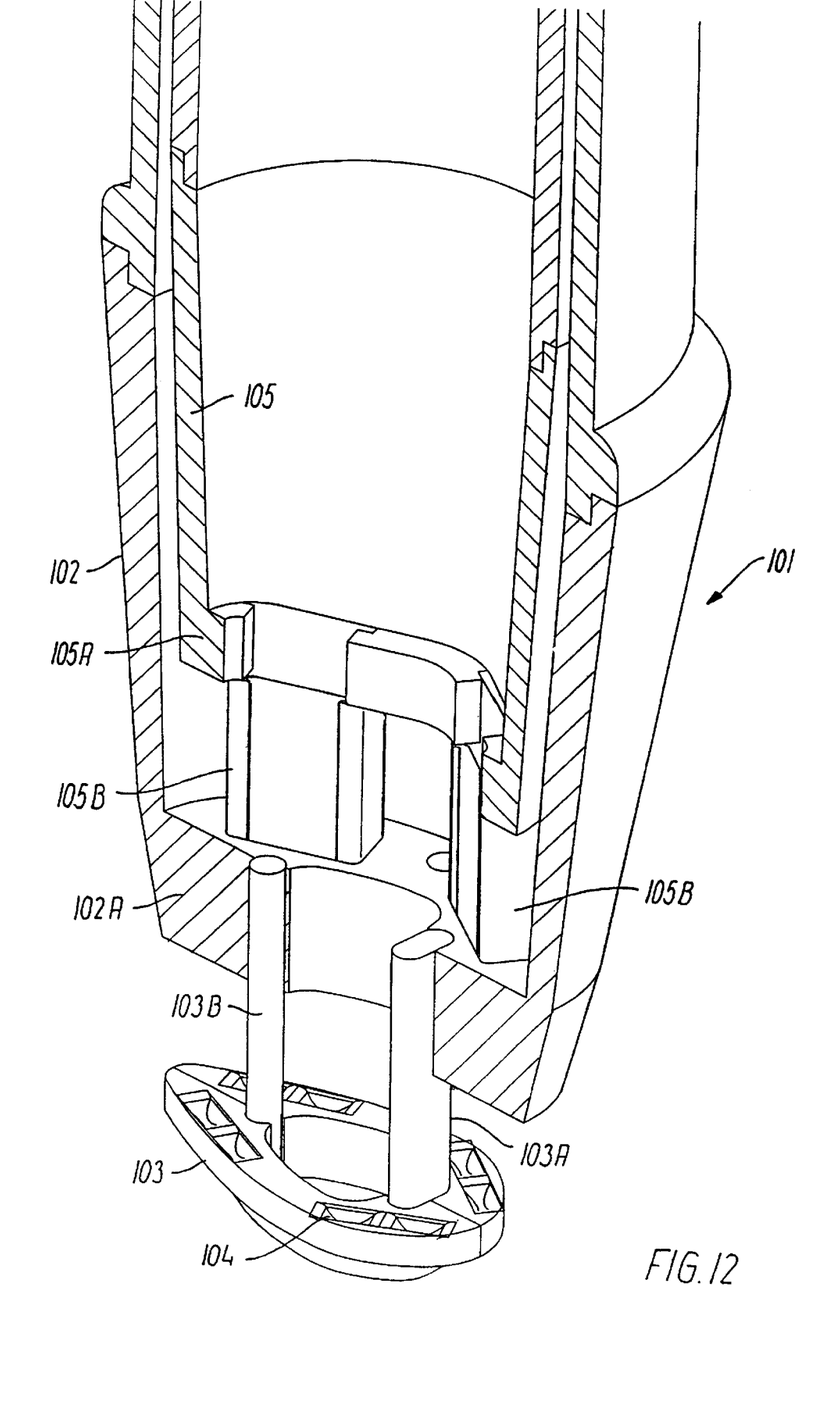
Figure 13:
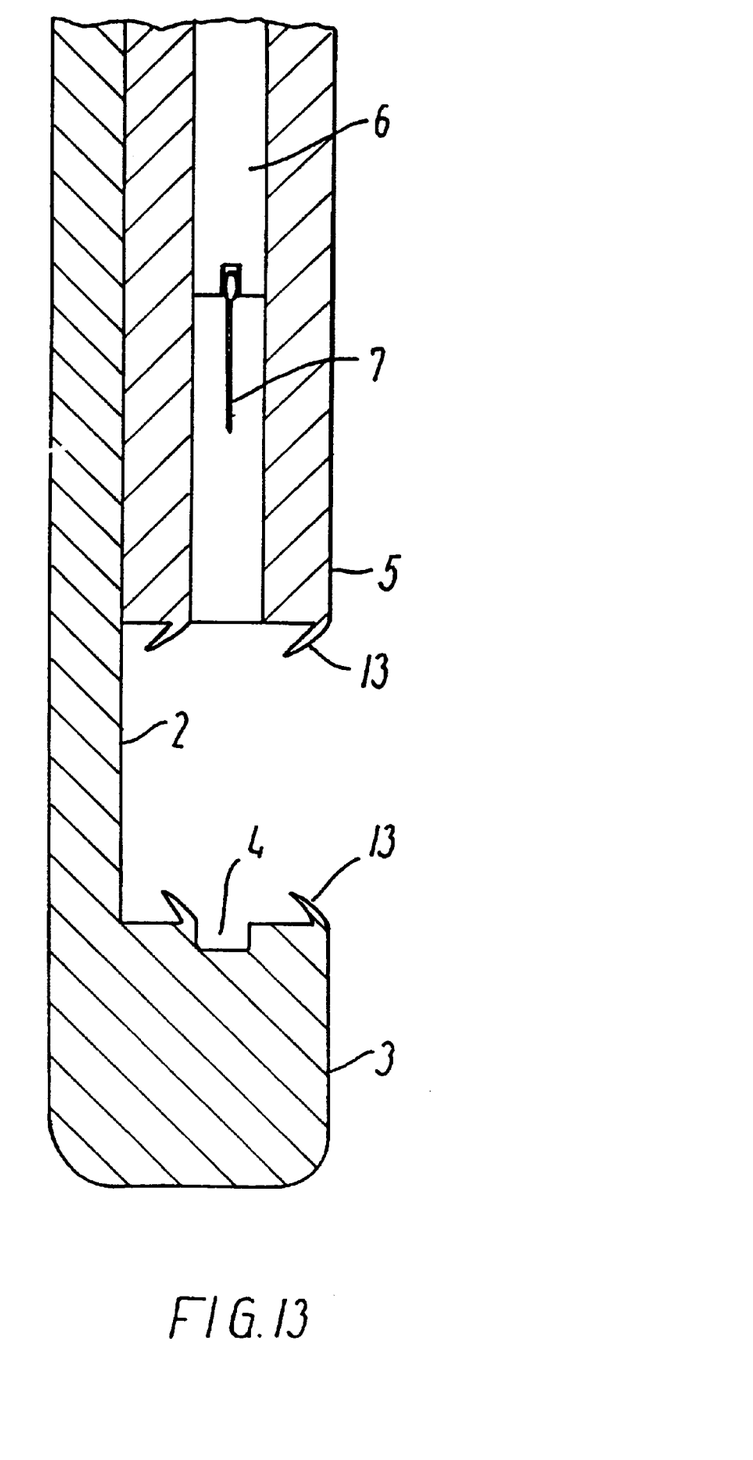

The relative positions shown in FIG. 12 correspond to those shown in FIGS. 6 and 7 and with the exception that in FIG. 12, the stapling plungers 106 have not only been withdrawn from the staples joining the two vessels, but have in fact been removed completely from the instrument to make it possible to insert a new set of staples, that may be of the disposable or semi-disposable type.

With the arrangement shown in FIGS. 9–12, the operating surgeon may literally have a firm grip on the situation by holding the outermost component, i.e. the anvil tube 102, which is rigidly connected to the anvil 103 through the columns 103A and 103B, so that he or she will be able to move the anvil 103 with the everted end of the bypass vessel into the opening in the coronary artery by direct manual control, and—not least—by "direct mechanical feedback", as the rigid mechanical interconnection between the anvil 103 og the anvil tube 102 enables the surgeon to "feel" whatever object is encountered by the anvil. Advantageously, the rearward (upper) part (not shown) of the instrument may comprise suitable operating devices and/or mechanisms for moving the clamping tube 105 and the stapling plungers 106 relatively to the anvil tube 102 and hence relatively to the anvil 103. Due to the extremely limited time available for performing coronary bypass operations, these operating devices and/or mechanisms should be designed to enable the operating surgeon to initiate the requisite movements rapidly and with a minimum of effort.

Thus, the operating devices and/or mechanisms could be arranged to function under the control of a single operating member, such as a push-button on the rear (upper) end of the instrument adapted to be operated by the surgeon's thumb, in the following manner:

firstly, when the operating member is moved in a first direction, e.g. a push-button is depressed, the clamping columns 105B will be advanced to their forwardmost (lower) position, in which they clamp the end region of the bypass vessel and the edge region of the opening in the artery together until said stop is reached, and then the stapling plungers 106 will immediately be actuated to staple the two regions together, after which both the clamping columns 105B and the stapling plungers 106 are withdrawn, e.g. by releasing said push-button, and secondly, immediately upon the operating member moving in the opposite direction, e.g. when the push-button has been released, the mechanism is re-set in readiness for a movement in the first direction, after which the instrument can be removed as described above with reference to FIG. 7.

The anastomotic instrument according to the present invention shown in FIGS. 14–18 possesses several features in commom with that of the previous application referred to initially and shown in FIGS. 11–13, especially FIGS. 9–12, this being the main reason for including a description of the previous embodiments in order to make it easier to understand the functioning of the instrument according to the present invention.

Figure 14:
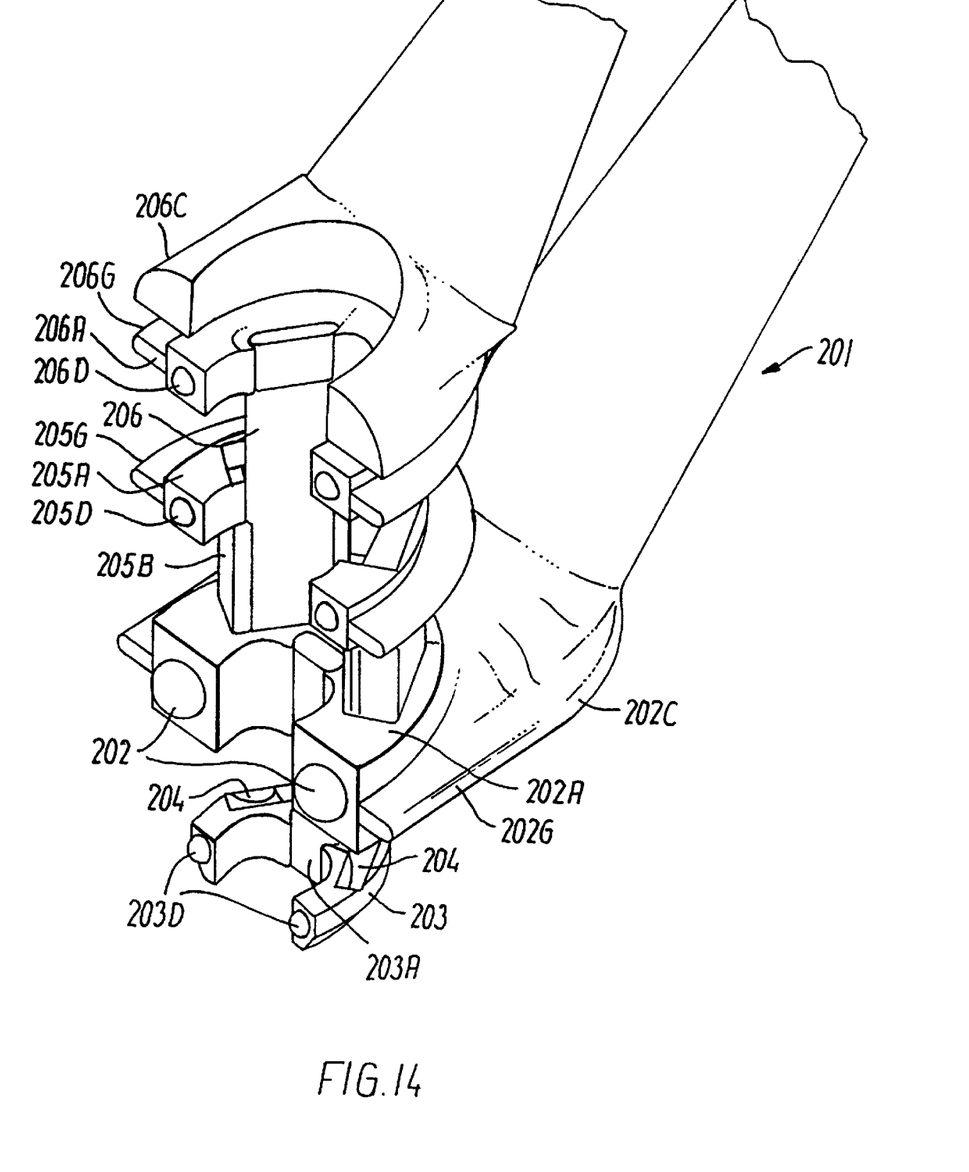
FIGS. 14–18 show the anastomotic instrument according to the present invention.

Looking at FIG. 14, showing some of the essential parts of the instrument, it will be seen that the instrument comprises a number of components with the same functions as those of the instrument shown in FIGS. 9–12. At this stage it should be noted that the instrument is adapted to be split along a longitudinal dividing plane, and FIG. 14 shows solely the parts on one side of this plane.

The reference numerals of the parts shown in FIGS. 14–18 are mostly the same as those of parts having similar functions down in FIGS. 9–12 with 100 or 200 added.

Figure 15:
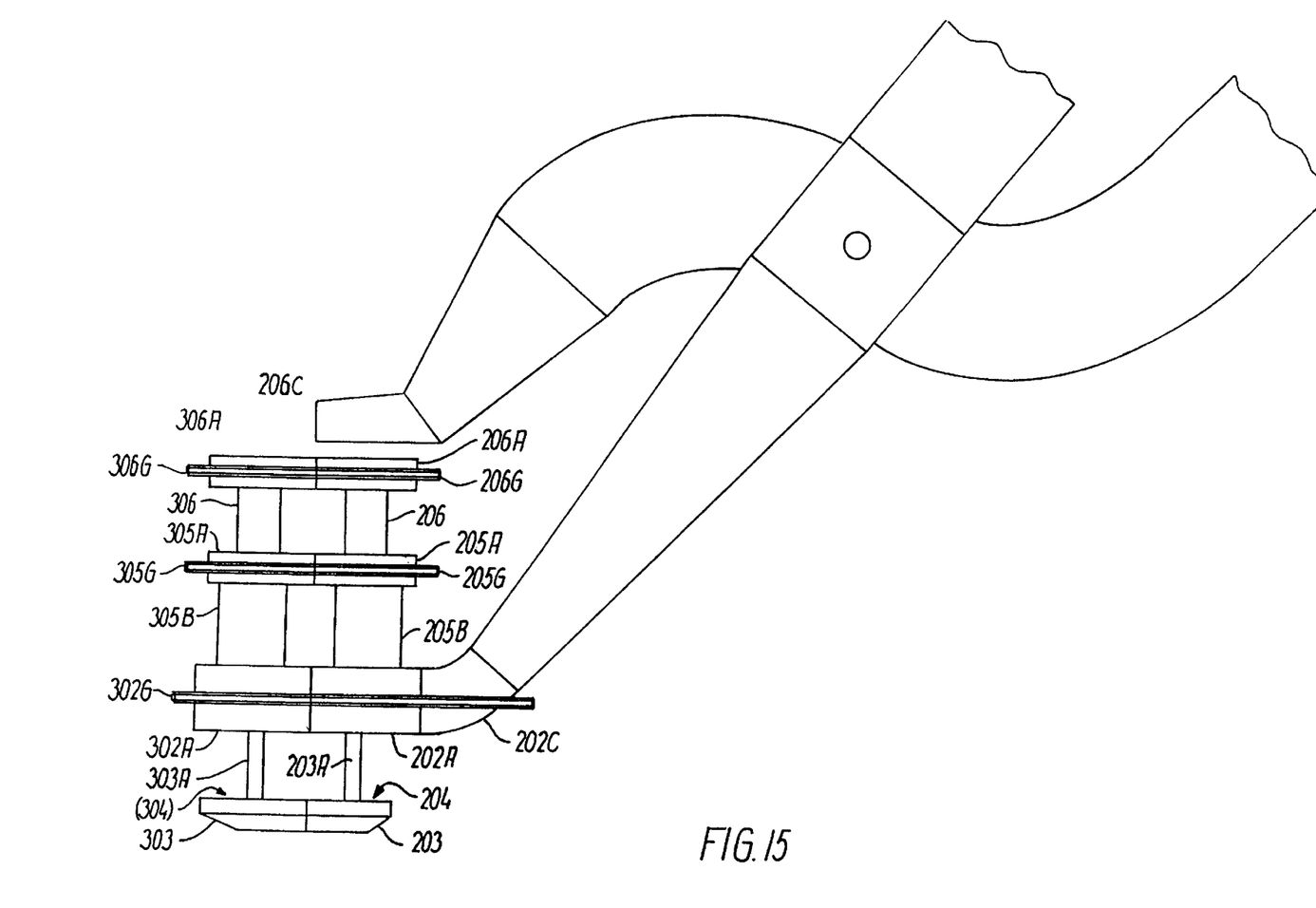

Thus, the parts shown in FIGS. 14–18 of the anastomotic instrument 201 of the present invention comprise a first rigid assembly or anvil assembly having an anvil carrier upstream half 202A, in operation being releasably connected to a similar anvil carrier downstream half 302A shown in FIG. 15 by means of two connecting knobs 202D engaging in suitable recesses (not visible) in said downstream half 302A, a lower jaw 202c of the instrument 201, the latter being shaped like a pair of tongs (vide FIG. 15), and an anvil upstream half 203 rigidly connected to the anvil carrier upstream half 202A through an anvil upstream column 203A and having two staple-bending recesses 204 as well as two connecting knobs 203D for releasable connection to an anvil downstream half 303 shown in FIG. 15.

This first rigid assembly generally corresponds to the assembly shown in FIGS. 9–12 comprising the anvil tube 102 with its end wall 102A and the anvil 103 with staple-bending recesses 104 and connected to said end wall 102A through two anvil columns 103A and 103B.

A second rigid assembly or clamping assembly, movable relative to said first rigid assembly, comprises a clamping column carrier consisting of an upstream half 205A and a downstream half 305A, releasably interconnected by means of connecting knobs 205D on said upstream half cooperating with recesses (not visible) in the downstream half, rigidly connected to the uppermost end of four upstream and downstream clamping columns 205B and 305B respectively, slidable in and extending through the respective anvil carrier halves 202A and 302A so as to be capable of being moved into abutment with the upper side of the anvil upstream and downstream halves 203 and 303 respectively in the same manner as shown in FIGS. 4 and 10 depicting the earlier instrument.

This second rigid assembly will be seen generally to to the assembly shown in FIGS. 9–12 comprising the clamping tube end wall 105A and the clamping columns 105B.

A third rigid assembly or stapling assembly, movable relative to said first (anvil) and second (clamping) rigid assemblies, comprises a stapling plunger carrier consisting of an upstream half 206A and a downstream half 306A, releasably interconnected by means of connecting knobs 206D on said upstream half cooperating with recesses (not visible) in the downstream half, rigidly connected to the uppermost ends of four upstream and downstream stapling plungers 206 and 306 respectively, slidable in guideways in the upstream and downstream clamping columns 205B and 305B respectively, thus extending through both the clamping carrier halves 205A and 305A and the anvil carrier halves 202A and 302A respectively, so as to make it possible to advance the stapling plungers 206 and 306 carrying staples (not shown) in their lowermost ends into cooperation with the staple-bending recesses 204 and 304 in the upper sides of the anvil halves 203 and 303 respectively in the same manner as shown in FIGS. 5 and 11 depicting the earlier instrument.

This third rigid assembly will be seen generally to correspond to the assembly shown in FIGS. 9–12 comprising the stapling plunger carrier 106A, and the stapling plungers 106.

After having read the explanation of the functioning of the examples shown in FIGS. 1–8 and 9–12 respectively, the reader should turn the attention to FIG. 15.

As will be evident from said explanation, the relative movements between the anvil assembly, the clamping assembly and the stapling assembly should take place in a certain sequence, i.e.

I moving the clamping assembly relative to the anvil assembly so as to make the clamping columns 205B and 305B clamp the tissue regions 10 and 12 (cf. FIG. 4) together, II moving the stapling assembly relative to the anvil assembly so as to staple the tissue regions 10 and 12 to each other (cf. FIG. 5), and III moving the clamping assembly and the stapling assembly together in the opposite directions relative to the anvil assembly so as to make it possible to liberate the instrument from the anastomosis having been established (cf. FIGS. 6–8).

A preferred feature of the present invention is the use of elastic means having different spring characteristics to effect these relative movements. The reader is asked to imagine two compression springs or sets of same, the first of which is placed between the clamping column carrier 205A, 305A and the anvil column carrier 202A, 302A and is relatively soft, i.e. needs relatively little force to be compressed, the second being placed between the stapling plunger carrier 206A, 306A and the clamping column carrier 205A, 305A and is relatively stiff.

Now, slowly squeezing the three assemblies between the lower jaw 202C and the upper jaw 206C will first compress relatively soft first spring between the clamping column carrier 205A, 305A and the anvil column carrier 202A, 302A, thus effecting the relative movement I above, i.e. the clamping movement (cf. FIG. 4)

When the clamping columns 205B and 305B have arrived at their clamping position, they cannot be moved further, and continued squeezing will cause compression of the second spring or set of springs between the stapling plunger carrier 206A, 306A and both the clamping and anvil assemblies, so that the stapling plungers will be moved according to the relative movement II above (cf. FIG. 5), thus completing the stapling operation and creating the anastomosis.

Finally, relaxing the grip will allow the springs to return the parts to the initial relative positions shown in FIG. 15 (cf. also FIGS. 6–8), so that the instrument may be removed in a manner corresponding to that shown in FIGS. 7 and 8.

The purpose of dividing the three assemblies in upstream and downstream halves is to make it possible firstly, with the upstream and downstream halves unified as shown in FIG. 15, to fit the instrument with a graft vessel (not shown) in a manner like that shown in FIG. 2, secondly, to establish the anastomosis in a manner like that shown in FIGS. 3–8, and thirdly, according to the present invention, to split the three assemblies lengthwise, so as to make it possible to remove the instrument from a graft vessel that—typically because it has already been anastomotized or has an anatomically fixed origin at the opposite end—cannot be pulled out of the assemblies (cf. FIGS. 7 and 8).

Figure 16:
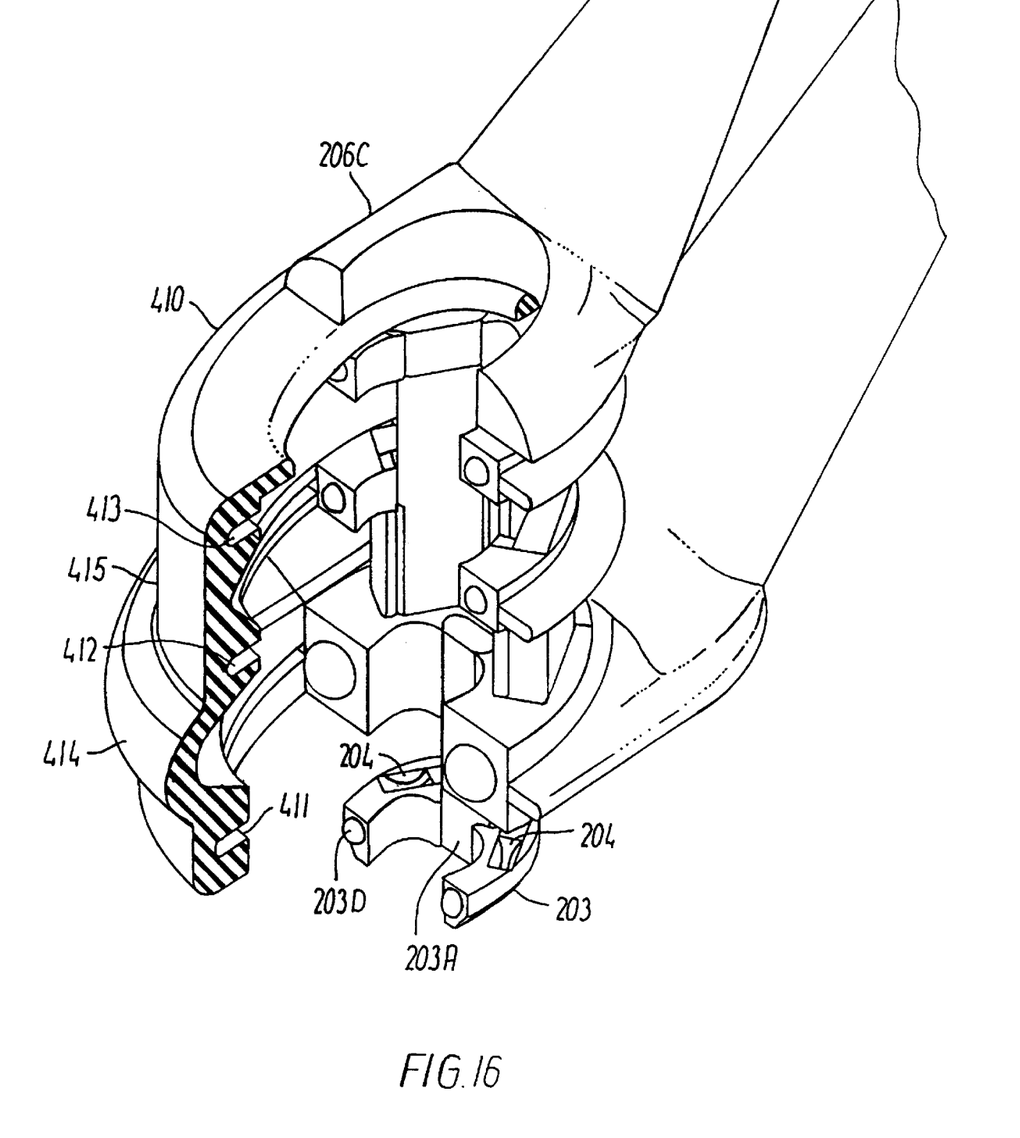
Figure 17:
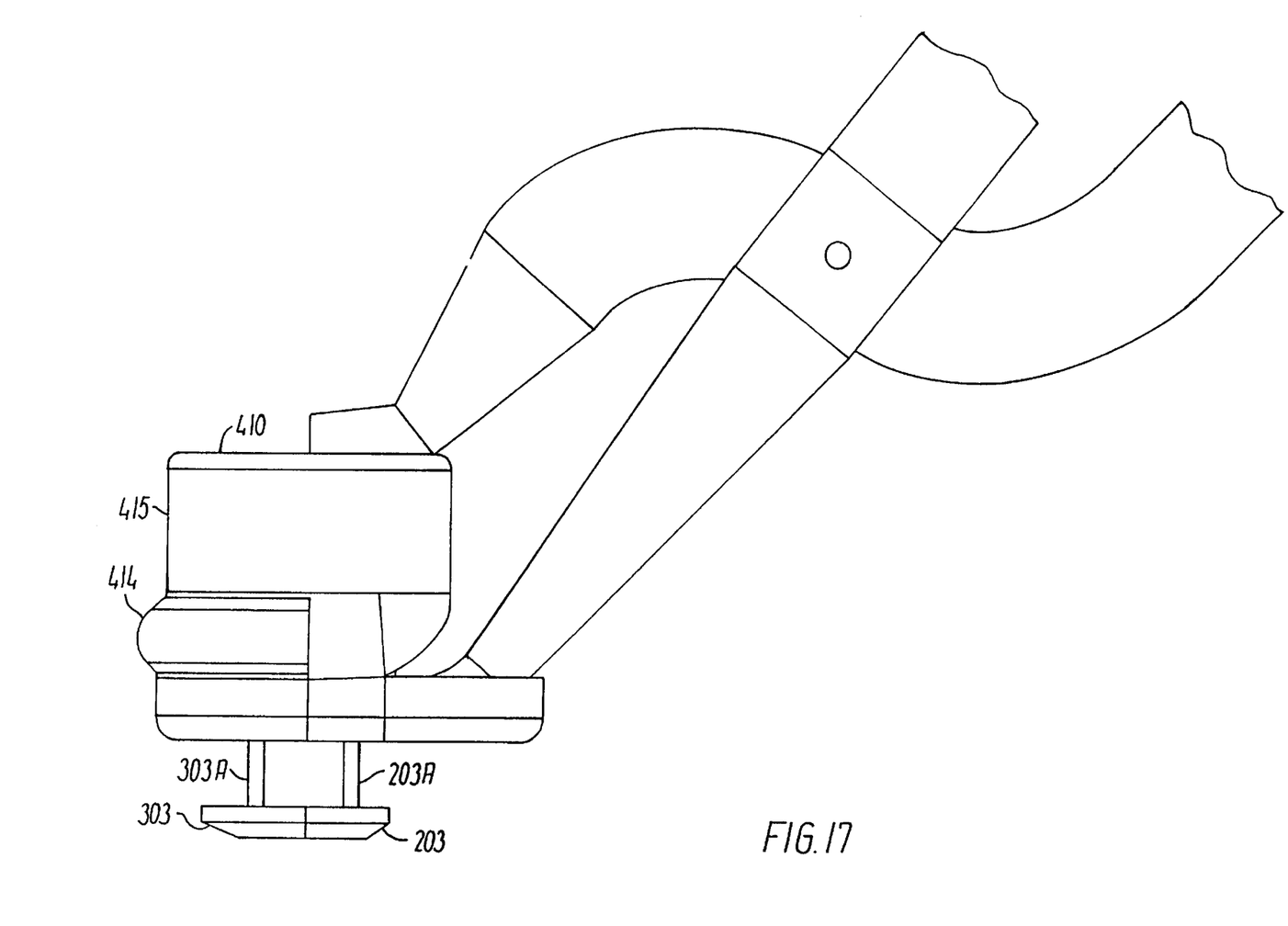
Figure 18:
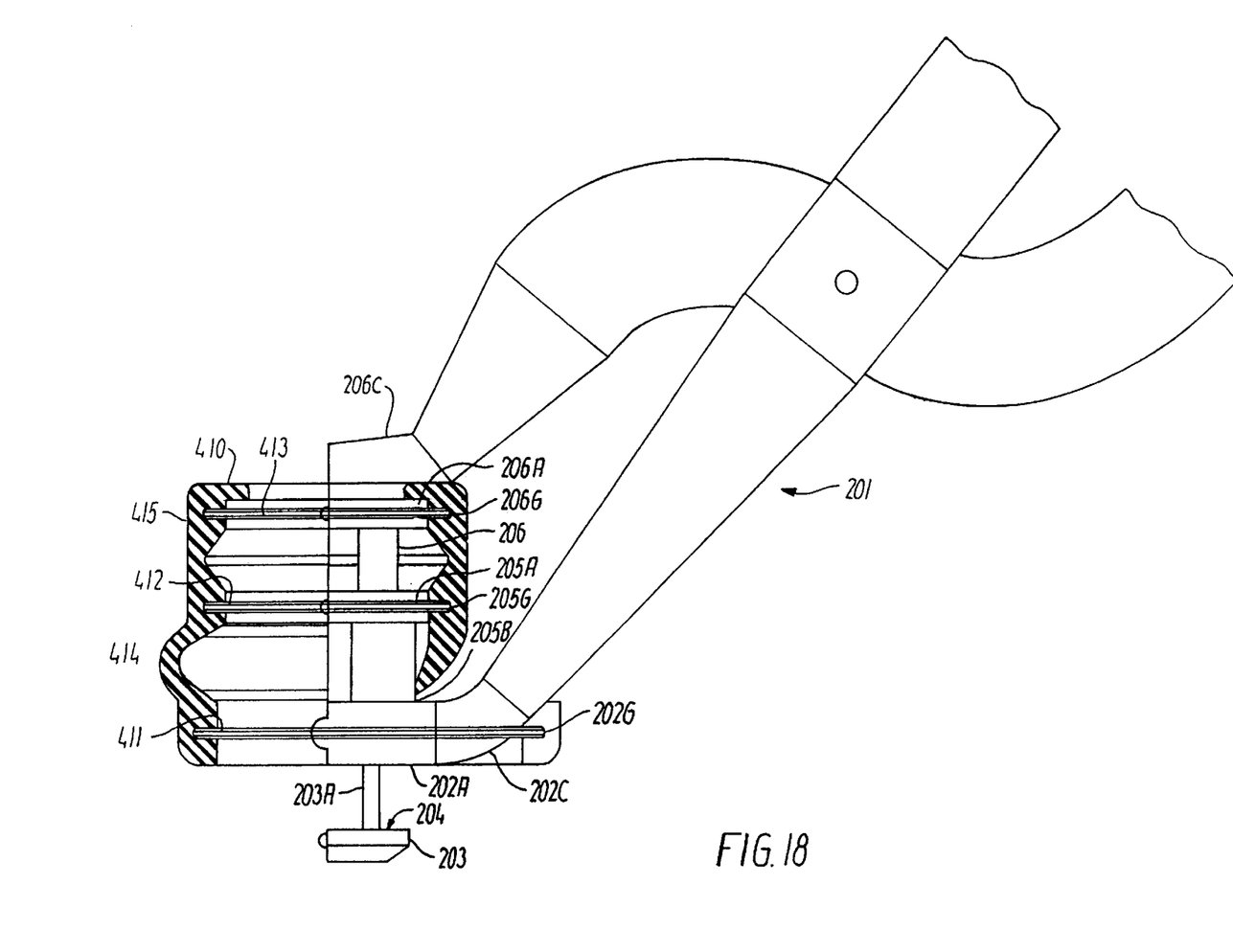

For the above purpose, the present invention preferably specifies the use of the elastic member 410 shown in FIGS. 16–18, best understood by also looking at FIGS. 14 and 15. This elastic member 410 serves three functions, viz.:

a) keeping the upstream and downstream halves of the three rigid assemblies together during the steps of fitting the instrument with a graft vessel and establishing the anastomosis, b) providing the different spring characteristics necessary for the various relative movements to take place in the correct sequence as explained above, and c) making it possible, in a manner to be explained, to separate the upstream and downstream parts from each other to enable them to be removed sideways from the graft vessel.

Thus, the embodiment of the elastic member 410 shown in FIGS. 16–18 constitutes a sheath of rubber or rubber-like material (in the following referred to as "rubber") embracing closely and in elastic tension the two anvil carrier halves 202A and 302A, the two clamping column carrier halves 205A and 305A, and the two stapling plunger carrier halves 206A and 306A, for this purpose having internal gripping grooves 411, 412 and 413 respectively cooperating with gripping flanges 202G, 302G, 205G, 305G, 206G and 306G respectively.

Thus, when properly assembled, the three relatively movable assemblies, i.e. the anvil assembly, the clamping assembly and the stapling assembly described above, together with the rubber sheath 410, present themselves as a unified solid body with the external appearance shown in FIG. 17. Thus, the rubber sheath 410 can serve function a mentioned above.

As will be evident from FIGS. 15 and 18, the rubber sheath 410 comprises two axially springy segments with different spring characteristics, viz.:

a relatively soft segment 414 between the gripping grooves 411 and 412 for the anvil carrier 202A, 302A and the clamping column carrier 205A, 305A respectively, and a relatively stiff segment 415 between said gripping groove 412 and the gripping groove 413 for the stapling plunger carrier 206A, 306A.

Thus, the rubber sheath 410 can also serve function b referred to above in the manner explained further above using imaginary springs as an example.

When the anastomosis has been established and the instrument is to be removed, the rubber sheath 410 is cut open lengthwise by means of a suitable cutting instrument capable of making a cut all the way through the sheath 410. Such a cutting instrument could be or comprise a knife with indents in the cutting edge for the three gripping flanges 202G, 205G and 206G and/or 302G, 305G and 306G. It is, however, preferred to use one or two cutting wires (not shown) placed on the internal surface of the sheath 410 and having pulling loops or the like (likewise not shown), making it possible to cut the sheath 410 open in a manner known from various types of sealed packages.

Thus, function c referred to above can also be achieved by using the rubber sheath 410 according to the present invention.

I claim:

1. Method of connecting an end region (10) of a first vessel (9) to the side of a second vessel (11) by carrying out an end-to-side anastomosis, said method being of the kind comprising the following steps a–d:
    a) forming an opening in the side of said second vessel (11),
    b) inserting in said opening an anastomosis instrument (201) carrying said first vessel (9) in a central longitudinal cavity and with said end region (10) everted about a circumferential member (203, 303) constituting a forward portion of said instrument (201) in such a manner, that the intima side of said end region (10) comes into contact with the intima side of said second vessel (11) at an edge region (12) of said opening,
    c) joining said end region (10) to said edge region (12) by inserting penetratingly therethrough and leaving therein a plurality of spiked members, and
    d) removing said instrument (201) from the joint formed between said first (9) and second (11) vessels,
    said steps a–d being carried out by
    e) the use of an anastomosis instrument (201) comprising
    e1) an anvil assembly (202A, 302A, 203, 303, 203A, 303A) comprising a circumferential anvil member (203, 303) and in which said first vessel (9) may be placed with its end region (10) everted about said anvil member (203, 303) with the terminal part of said end region facing rearwardly, said anvil assembly being capable of being divided and the divided parts separated along said central longitudinal cavity,
    e2) rearwardly facing staple-bending recesses (204, 304) provided in said anvil member (203, 303),
    e3) a clamping assembly (205A, 305A, 205B, 305B) movable relative to said anvil assembly and comprising clamping members (205B, 305B) adapted to be moved towards said anvil member (203, 303) so as to make it possible to clamp together therebetween said end region (10) on said first vessel (9) and an edge region (12) on said second vessel (11), and
    e4) a stapling assembly (206, 306, 206A, 306A) comprising stapling plungers (206, 306) movable relative to said anvil assembly and said clamping assembly and adapted to insert staples (7) penetratingly through said clamped end (10) and edge (12) regions into engagement with said stapling-bending recesses (204, 304) so as to bend permanently said staples (7) into a shape, in which they hold said end (10) and edge (12) regions together,
    characterized by
    f) the use of an instrument (201), in which in addition to said anvil assembly, said clamping and stapling assemblies are capable of being divided and the divided parts separated along said central longitudinal cavity extending generally in the direction of relative movement of said three assemblies and dividing said assemblies in a manner allowing the separated parts to be removed from said first vessel (9) in a transverse direction.

2. Method according to claim 1, characterized by the use of a common sheath-like circumferentially elastic member (410) of rubber or rubber-like material placed in circumferentially elastic tension about said separable parts of said anvil, clamping and stapling assemblies.

3. Method according to claim 1, characterized by the use of an instrument (201) comprising
    a) a first, relatively soft compressionally elastic member (414) between said anvil and said clamping assemblies,
    b) a second, relatively stiff compressionally elastic member (415) between said clamping and said stapling assemblies, and
    c) a manually operable implement (202C, 206C etc.) adapted to press said stapling and said anvil members towards each other.

4. Method according to claim 2, characterized by the use of an instrument (201, in which said first (414) and second (415) compressionally elastic members constitute integral parts of the sheath-like circumferentially elastic member (410) of rubber or rubber-like material.

5. Anastomotic instrument (201) for connecting an end region (10) of a first vessel (9) to the side of a second vessel (11) by carrying out an end-to-side anastomosis comprising the following steps a–d:
    a) forming an opening in the side of said second vessel (11),
    b) inserting in said opening an anastomosis instrument (201) carrying said first vessel (9) in a central longitudinal cavity and with said end region (10) everted about a circumferential member (203, 303) constituting a forward portion of said instrument (201) in such a manner, that the intima side of said end region (10) comes into contact with the intima side of said second vessel (11) at an edge region (12) of said opening,
    c) joining said end region (10) to said edge region (12) by inserting penetratingly therethrough and leaving therein a plurality of spiked members, and
    d) removing said instrument (201) from the joint formed between said first (9) and second (11) vessels,
    said instrument comprising
    e) an anvil assembly (202A, 302A, 203, 303, 203A, 303A) comprising a circumferential anvil member (203, 303) and in which said first vessel (9) may be placed with its end region (10) everted about said anvil member (203, 303) with the terminal part of said end region facing rearwardly, said anvil assembly being capable of being divided and the divided parts separated along said central longitudinal cavity,
    f) rearwardly facing staple-bending recesses (204, 304) provided in said anvil member (203, 303),
    g) a clamping assembly (205A, 305A, 205B, 305B) movable relative to said anvil assembly and comprising clamping members (205B, 305B) adapted to be moved towards said anvil member (203, 303) so as to make it possible to clamp together therebetween said end region (10) on said first vessel (9) and an edge region (12) on said second vessel (11), and
    h) a stapling assembly (206, 306, 206A, 306A) comprising stapling plungers (206, 306) movable relative to said anvil assembly and said clamping assembly and adapted to insert staples (7) penetratingly through said clamped end (10) and edge (12) regions into engagement with said stapling-bending recesses (204, 304) so as to bend permanently said staples (7) into a shape, in which they hold said end (10) and edge (12) regions together, and characterized in e) that, in addition to said anvil assembly, said clamping and stapling assemblies are capable of being divided and the divided parts separated along said central longitudinal cavity extending generally in the direction of relative movement of said three assemblies and dividing said assemblies in a manner allowing the separated parts to be removed from said first vessel (9) in a transverse direction.

6. Anastomotic instrument according to claim 5, characterized by a common sheath-like circumferentially elastic member (410) of rubber or rubber-like material placed in circumferentially elastic tension about said separable parts of said anvil, clamping and stapling assemblies.

7. Anastomotic instrument according to claim 5, characterized by a) a first, relatively soft compressionally elastic member (414) between said anvil and said clamping assemblies, b) a second, relatively stiff compressionally elastic member (415) between said clamping and said stapling assemblies, and c) a manually operable implement (202C, 206C etc.) adapted to press said stapling and said anvil members towards each other.

8. Anastomotic instrument according to claim 7, characterized in that said first (414) and second (415) compressionally elastic members constitute integral parts of the sheath-like circumferentially elastic member (410) of rubber or rubber-like material.

9. Anastomotic instrument according to claim 6, characterized by at least one flexible cutting wire placed on the internal surface of said sheath-like circumferentially elastic member (410) and having a pulling loop or the like making it possible to cut said member (410) open by pulling said pulling loop or the like.

* * * * *